(12) United States Patent
Kokubo et al.

(10) Patent No.: US 8,475,826 B2
(45) Date of Patent: Jul. 2, 2013

(54) TITANIUM OXIDE-ORGANIC POLYMER CONJUNCTION SUITABLE FOR ARTIFICIAL BONE

(75) Inventors: Tadashi Kokubo, Kyoto (JP); Masakazu Kawashita, Kyoto (JP); Takashi Nakamura, Kyoto (JP)

(73) Assignee: Japan Science & Technology Agency, Saitama (JP)

( * ) Notice: Subject to any disclaimer, the term of this patent is extended or adjusted under 35 U.S.C. 154(b) by 9 days.

(21) Appl. No.: 12/796,636

(22) Filed: Jun. 8, 2010

(65) Prior Publication Data
US 2010/0247739 A1 Sep. 30, 2010

Related U.S. Application Data

(63) Continuation of application No. 10/560,744, filed as application No. PCT/JP2004/004406 on Mar. 29, 2004, now abandoned.

(30) Foreign Application Priority Data

Jul. 11, 2003 (JP) ................................. 2003-293611

(51) Int. Cl.
```
A61F 2/28     (2006.01)
A61F 13/00    (2006.01)
A61L 27/06    (2006.01)
B05D 5/00     (2006.01)
A61K 33/24    (2006.01)
A61K 31/28    (2006.01)
```
(52) U.S. Cl.
USPC ............ 424/423; 424/422; 424/617; 514/492

(58) Field of Classification Search
USPC ................. 424/614, 617, 423, 422; 427/2.24, 427/2.27; 623/23.6, 23.61; 514/492
See application file for complete search history.

(56) References Cited

U.S. PATENT DOCUMENTS
2004/0126406 A1 * 7/2004 Kokubo et al. ............... 424/423

FOREIGN PATENT DOCUMENTS
WO WO 02089864 A1 * 11/2002

OTHER PUBLICATIONS

JP 2002-248163 Abstract, Mar. 2002, Patent Abstracts of Japan, pp. 1-7.*
JP 2002-248163, Internet Translation as English equivalent, 9 pages.*

* cited by examiner

Primary Examiner — John Pak
Assistant Examiner — Andriae M Holt
(74) Attorney, Agent, or Firm — Hahn & Voight PLLC

(57) ABSTRACT

The titanium oxide-organic polymer composite material for artificial bone obtained by forming titania gel on the surface of said base material by titania solution treatment to dip into a solution of 0° C. to 50° C. temperature for from several seconds to 1 week obtained by adding a solution consisting of acidic alcohol and water into alcohol solution of titaniumtetraalcoxide to a base material composed of a polymer compound selected from a group consisting of polyolefin, polyester and nylon, and modifying to a titanium oxide membrane which forms apatite having similar Ca/P atom ratio to an apatite of mammalian's bone in supersaturated aqueous solution to apatite or from a body fluid of mammalian by dipping said base material on the surface of which titania gel is formed into hot water of. 50° C. to 95° C. or solution of room temperature to 95° C. to which acid is added.

15 Claims, 4 Drawing Sheets

Titania Solution Treatment

Warm Water Treatment

Thin film X-ray diffraction pattern of PE, PET, EVOH and Nylon 6 after treated by titania-warm water, then dipped in SBF for 7 days

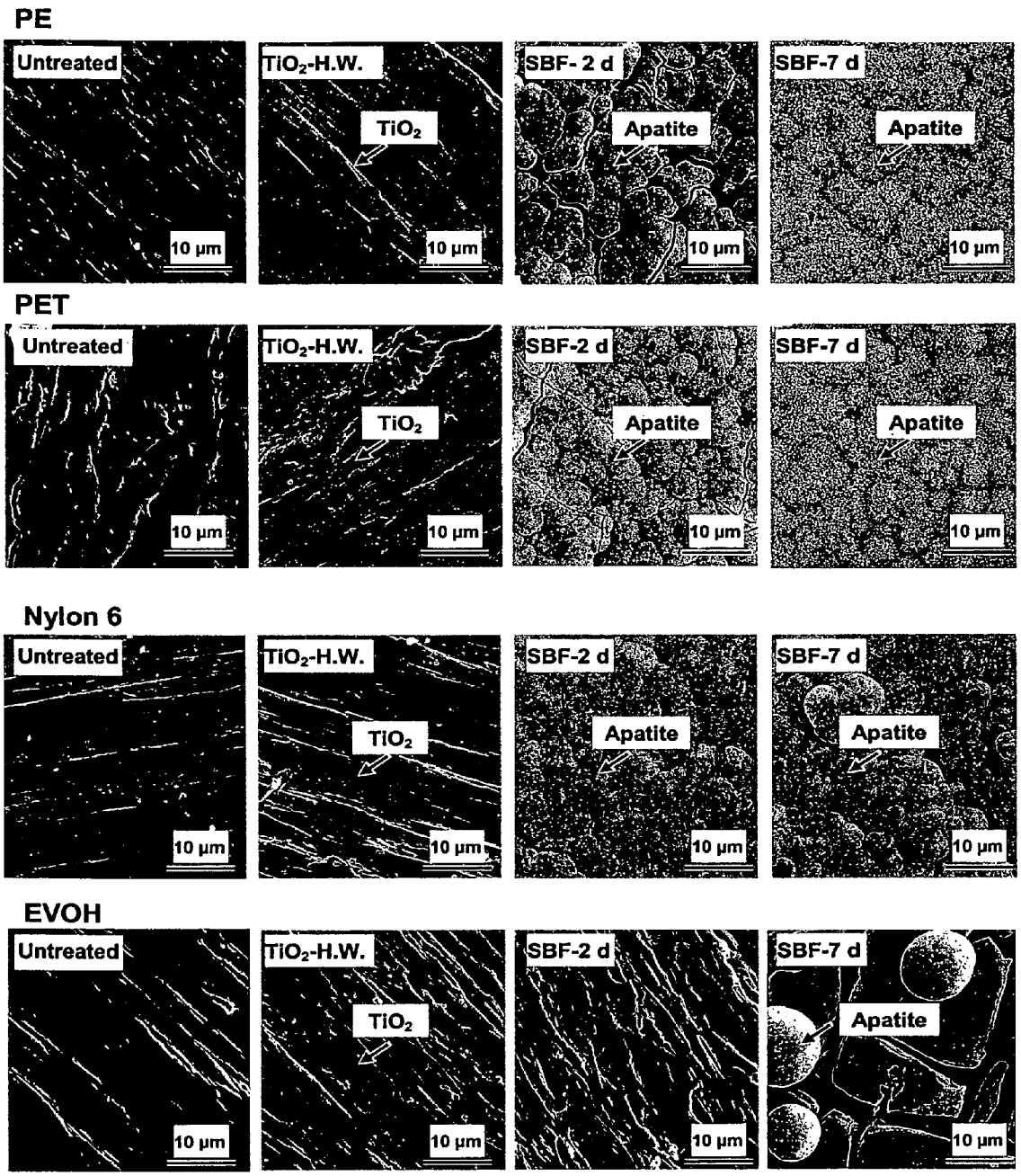
Fig. 4 FE-SEM photographs of the surfaces of PE, PET, Nylon 6 and EVOH treated with TiO$_2$ solution and hot water (H.W.) and subsequently soaked in SBF for 7 d.

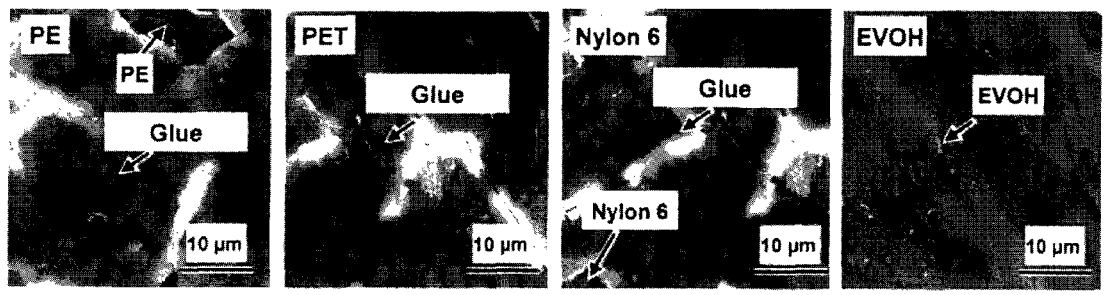
Fig. 5  FE-SEM photographs of the surfaces of samples after the peeling test with Scotch® tape (without silane-coupling treatment).

TITANIUM OXIDE-ORGANIC POLYMER CONJUNCTION SUITABLE FOR ARTIFICIAL BONE

FIELD OF THE INVENTION

The present invention relates to a titanium oxide-organic polymer composite material for an artificial bone prepared by using polyolefin, polyester or polyamide as a substrate, treating the surface of said substrate by titania solution directory then dipping it in warm water or solution to which acid is added whose temperature is from room temperature to 95° C., forming a titanium oxide membrane having a forming ability of apatite of similar Ca/P atom ratio as to apatite of mammalian's bone in supersaturated aqueous solution to apatite or in body fluid of mammalian.

BACK GROUND OF THE ART

Researches for a composite materials used for an artificial bone forming a layer of inorganic material which can form an apatite layer from a simulated body fluid (SBF), using an organic polymer containing ester group and/or hydroxyl group which has high apatite forming ability in a simulated body fluid (SBF), in other words, being familiar for formation of a layer whose bioactivity is high, for example, ethylene-vinylalcohol copolymer (hereinafter shortened to EVOH) possessing strength necessary as a bone on the surface of the organic polymer, have been carried out vigorously.

In said circumference, researches aiming to form easily a layer having high bioactivity on surface of a base material are also carried out. Especially, in a case to use an organic polymer not having a functional group which is advantageous for formation of a layer of said bioactivity, the formation of an intermediate layer to which bioactivity is provided is considered to be necessary. Further, as a composite material which forms said intermediate layer, a substrate material which is prepared and denatured by reacting 3-isocianatepropyltri-ethoxysilane [$OCN(CH_2)_3 Si(OCH_2H_5)_3$](hereinafter shortened to IPTS) and silica solution is proposed, furthermore, the treatment of surface by calcium silica solution is proposed.

Regarding said prior art, in M. Uchida, H.-M. Kim, T. Kokubo, S. Fujibayashi, T. Nakamura J. Biomed. Mater; Res., 64A (2003) 164-170 (Document 1), the fact that Ti—OH group in titania gel having specific structure, such as anatase, causes formation of apatite nucleus in short term in SBF is reported. Further, it is reported that when the surface of said base material is treated by IPTS and further treated by calcium silicate solution, obtained specimen forms apatite on the surface in SBF within 2 days, however, since the formed calcium silicate gel layer dissolves rapidly in SBF, it is very difficult to control the formation of apatite on the surface of the specimen. On the contrary, since the solubility of titania gel to SBF is remarkably small, the titania gel layer having Ti—OH group is excellent as a bioactivity layer.

Still further, in JP 2002-325834 publication (Document 2), especially in claims, [0012] and [0013], an invention of a titanium oxide-organic polymer composite material for an artificial bone obtained by following process is reported. That is, after forming titania gel on the surface of a base material substantially composed of organic polymer, by transforming to a titanium oxide membrane having activity to form an apatite of Ca/P atomic ratio same as to an apatite of bone of a mammal from body fluid of a mammal by treating said titania gel with warm water or aqueous solution of acid. However, this document reports that, as a polymer consisting of a base material which can form the titanium oxide membrane having an activity to form an apatite without forming an intermediate layer, it is necessary to use a polymer containing hydroxyl group and/or derivatives thereof, thiol group, aldehyde group or amino group [0013].

Therefore, said composite material for an artificial bone is required to use a polymer having said active group as a polymer to consist of a base material, or to be treated so as to form an intermediate layer which makes possible to form a bioactivity layer.

The subject of the present invention is to provide a titanium oxide-organic polymer composite material for an artificial bone obtained by using a polymer which does not have above mentioned active group as a material which composes a base material for an artificial bone, further not forming said intermediate layer.

For the purpose to accomplish the subject of the present invention, an investigation to obtain a titanium oxide-organic polymer composite material for artificial bone using polyolefin, especially polyethylene, in particular low-density polyethylene, polyester, especially polyethyleneterephthalate, nylon, especially 6 nylon, is carried out without forming said intermediate layer, and combinations of a specimen obtained from materials consisting of said base material, material for forming bioactive titanium oxide layer and forming conditions of a titanium oxide-organic polymer composite material for artificial bone are investigated by trial and error. As understood from Examples and Comparative Examples which uses EVOH, which will be illustrated after, an unexpected result is obtained in a case in which specific material polymer is used. That is, it is confirmed that a titanium oxide layer formed on the surface of the base material has high bioactivity further has high resistance to peeling confirmed by a peeling test using an adhere tape, and above mentioned subject is accomplished. Said titanium oxide layer is formed by a process mentioned in Patent Document 1 which was filed by the inventors of the present invention by processing a material consisting a base material by "forming titania gel on the surface of said base material by titania solution treatment characterizing dipping into a solution of 0° C. to 50° C. temperature for from several seconds to 1 week obtained by adding a solution consisting of acidic alcohol and water into alcohol solution of titaniumtetraalcoxide, and by dipping said base material on the surface of which titania gel is formed into hot water of 50° C. to 95° C. or solution of room temperature to 95° C. to which acid is added".

DISCLOSURE OF THE INVENTION

The first one of the present invention is (1) a titanium oxide-organic polymer composite material for artificial bone obtained by forming titania gel on the surface of said base material by titania solution treatment to dip into a solution of 0° C. to 50° C. temperature for from several seconds to 1 week obtained by adding a solution consisting of acidic alcohol and water into alcohol solution of titaniumtetraalcoxide to a base material composed of a polymer compound selected from a group consisting of polyolefin, polyester and nylon, and modifying to a titanium oxide membrane which forms apatite having similar Ca/P atom ratio to an apatite of mammalian's bone in supersaturated aqueous solution to apatite or from a body fluid of mammalian by dipping said base material on the surface of which titania gel is formed into hot water of 50° C. to 95° C. or solution of room temperature to 95° C. to which acid is added. Desirably, the first one of the present invention is (2) the titanium oxide-organic polymer composite material for artificial bone of (1), wherein titaniumtetraalcoxide is tetraisopropyltitanate, alcohol is ethanol and acid is inorganic acid, more desirably the first one of the present invention is (3) the titanium oxide-organic polymer composite material for artificial bone of (1) or (2), wherein polyolefin is low-density polyethylene, polyester is polyethyleneterephthalate and nylon is 6-nylon, further desirably the first one of the present invention is (4) the titanium oxide-organic polymer composite material for artificial bone of (1), (2) or (3), wherein the solution for titania solution treatment is prepared by dipping a solution composed of acidic alcohol and water to a solution of titaniumtetraalcoxide and alcohol maintaining the temperature to 0° C. to 10° C., especially, maintaining said temperature using water with ice.

The second one of the present invention (5) is a composite for artificial bone prepared by obtaining a titanium oxide-organic polymer composite material for artificial bone obtained by forming titania gel on the surface of said base material by titania solution treatment characterizing dipping into a solution of 0° C. to 10° C. temperature for from several seconds to 1 week obtained by adding a solution consisting of acidic alcohol and water into alcohol solution of titaniumtetraalcoxide to a base material composed of a polymer compound selected from a group consisting of polyolefin, polyester and nylon, and modifying to a titanium oxide membrane which forms apatite having similar Ca/P atom ratio to an apatite of mammalian's bone in supersaturated aqueous solution to apatite or from a body fluid of mammalian by dipping said base material on the surface of which titania gel is formed into hot water of 50° C. to 95° C. or solution of room temperature to 95° C. to which acid is added, then forming an apatite by dipping said composite into supersaturated aqueous solution to apatite, desirably the second one of the present invention (6) is the composite material for artificial bone of (5), wherein titaniumtetraalcoxide is tetraisopropyltitanate, alcohol is ethanol and acid is inorganic acid, more desirably the first one of the present invention is (7) the composite material for artificial bone of (5) or (6), wherein titanium oxide-organic polymer for artificial bone is obtained by using low-density polyethylene as polyolefin, polyethyleneterephthalate as polyester and 6-nylon as nylon, further desirably the first one of the present invention is (8) the titanium oxide-organic polymer composite material for artificial bone of (5), (6) or (7), wherein the solution for titania solution treatment is prepared by dipping a solution composed of acidic alcohol and water to a solution of titaniumtetraalcoxide and alcohol maintaining the temperature to 0° C. to 10° C.

Another embodiment of the invention is a method for producing a titanium oxide-organic polymer composite material for artificial bone comprising the steps of:

forming a titania solution by adding a solution consisting of acidic alcohol and water into an alcohol solution of titaniumtetraalkoxide, providing an organic polymer base material which includes a polymer selected from the group consisting of polyolefin, polyester and nylon, and does not have an active group selected from the group consisting of hydroxyl groups or derivatives thereof, thiol groups, aldehyde groups and amino groups, forming titania gel on the surface of the base material by dipping the base material into a solution of the titania solution which is at a temperature of 0° C. to 50° C. for several seconds to 1 week and drying the base material with the titania gel formed on its surface, treating the titania gel that has formed on the surface of the base material by dipping the base material with the titania gel formed on its surface into hot water of 50° C. to 95° C. or a solution of room temperature to 95° C. to which acid is added for an effective period of time to form a titanium oxide membrane on the base material and to obtain the titanium oxide-organic polymer composite material for artificial bone, wherein the titanium oxide membrane has activity to form an apatite in mammalian body fluid, and wherein the apatite has a similar Ca/P atom ratio to an apatite of mammalian bone, with the proviso that an intermediate layer is not formed on the base material by contacting the base material with a silane coupling agent to form an intermediate layer.

BRIEF DESCRIPTION OF THE DRAWINGS

FIG. 4 is a FE-SEM (Field Emission Scanning Electron Microscope) picture showing a specimen treated by titania solution-warm water of FIG. 1 and apatite formation characteristic after dipped in SBF (2 days and 7 days).

FIG. 5 is a FE-SEM (Field Emission Scanning Electron Microscope) picture of the apatite formed specimen after removing test by a Scotch Tape (T.M.).

DESCRIPTION OF THE PREFERRED EMBODIMENT

The present invention will be illustrated more in detail.
A. As a material for substrate, a polymer compound selected from a group consisting of polyolefin, polyester and Nylon can be used. In particular, low-density polyethylene (Product of Sumitomo Kagaku Co., Ltd.), polyethyleneterephthalate (PET, Product of Toyo Kasei Co., Ltd.) and 6-Nylon (Product of Scientific Polymer Products Co., Ltd.) can be mentioned as desirable ones. As a specimen (S) to confirm the usefulness as an artificial bone, a substrate of $10 \times 10 \times 1$ mm$^3$ is prepared and used.

As a base material, any kinds of structural feature such as block, sheet, fiber, tape, filament or yarn can be used, further, a secondary processed products of these materials, for example, woven cloth (including three dimensional woven cloth), non-woven cloth or sliver can be used and can provide a shape which improve a characteristic as an artificial bone for reinforce.

Figure 1:
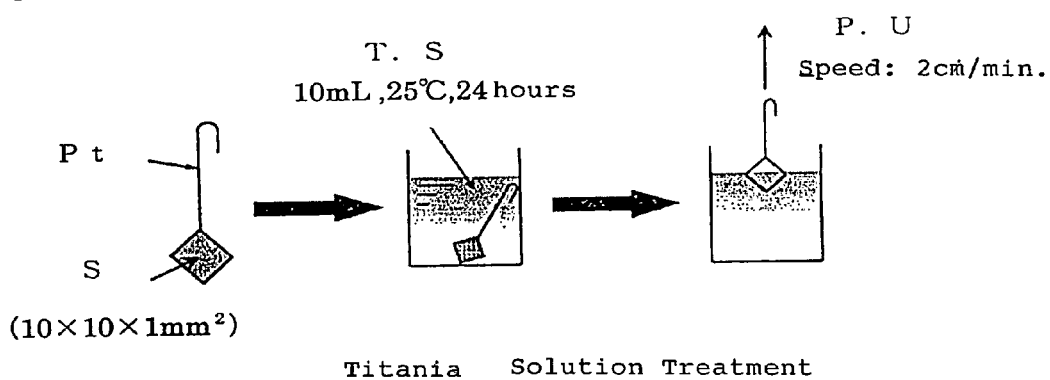
FIG. 1 is a drawing to illustrate a process for treatment by dipping a specimen (S) characterized by fuse adhering a platinum wire to one corner of a specimen substrate into titania solution (T.S) and pulling up (P.U) by prescribed speed.

B. Titania treatment to form a titania membrane;
Process for titania treatment is shown in FIG. 1.

To one corner of a specimen substrate prepared in A, a platinum code (Pt) is fuse adhered.

Titania solution is prepared by following process, that is, to a solution containing $Ti(OiC_3H_7)_4$ (TiPT) and half amount of $C_2H_5OH$, which is maintained at the temperature between 0° C. and 10° C., adds solution containing residue half amount of $C_2H_5OH$, $HNO_3$ and $H_2O$ by dropping it slowly under the condition to maintain the temperature to 0° C. to 10° C., for example, by cooling with ice. Ratio of materials is as follows;

Ti(OiC$_3$H$_7$)$_4$; H$_2$O:C$_2$H$_5$OH: HNO$_{3=1.0:0.1}$-10:1-100: 0.01-10 (by molar ratio)

Said specimen is dipped in the prepared titania solution at 0° C. to 50° C., for example, at 25° C., for from several seconds to one week, for example, 24 hours. After that, the specimen is pulled up by pulling up speed of 0.1-10 cm/minute, for example, 2 cm/minute. The specimen is dried at the temperature from 30° C. to 150° C. in a dryer (in air, product of YAMATO Co., Ltd., DK-600) for 24 hours.

C. Treatment to Provide Apatite Forming Ability to a Titania Gel Layer prepared in the process B.

This treatment is to form a titania membrane possessing Ti—OH group in fine crystal of anatase or brookite by treating titania gel with warm water or acid aqueous solution, and is desirable to be carried out under acidic condition of pH lower than 7 and/or term of 1 hour to 1 month and/or temperature of 30° C. to 120° C., especially in warm water of 50° C. to 95° C., or solution of room temperature to 95° C. to which acid is added. That is, it is important to select and combine said conditions.

Figure 2:
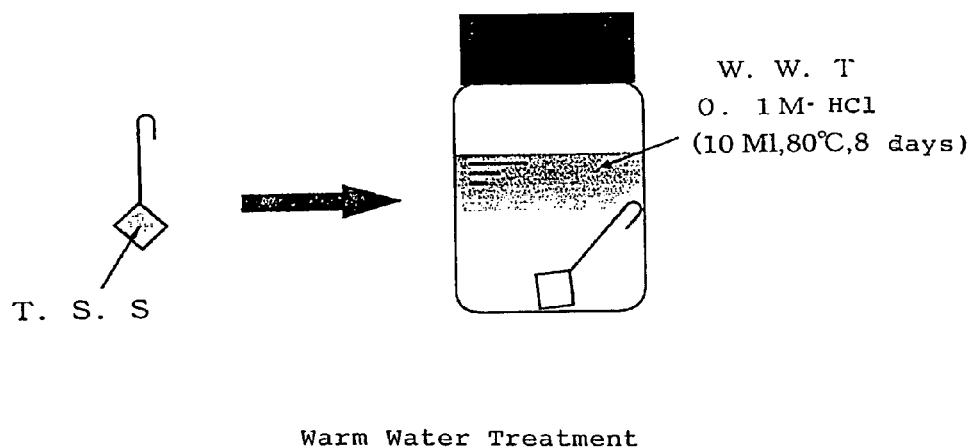
FIG. 2 is a drawing to illustrate a process which treat a specimen (T.S.S) treated by the process of FIG. 1 with warm water (W.W.T).

A case for treatment using HCl aqueous solution as an inorganic acid solution is indicated (FIG. 2). For example, the specimen treated by the process B is treated by dipping in 0.1M HCl aqueous solution at 80° C. for 8 days.

D. Treatment by Titania Solution

Surface structure change of various polymers which are treated by titania solution and warm water is analyzed using various measuring instruments mentioned below.

1. Field Emission Scanning Electron Microscope (FE-SEM); Product of Hitachi Seisakusho Co., Ltd., S-4700.
2. Energy Dispersive X-ray Spectrometer (EDX); Product of Horiba Seisakusho Co., Ltd., EMAX-7000
3. X-ray Photoeletron Spectroscope (XPS: MT-5500, product of ULVAC-PHI Co., Ltd.)
4. Thin-Film X Ray Diffractometer (TF-XRD: RINT2500, Product of Rigaku Co., Ltd.)
5. Measurement of adhesive strength of Titania Thin Film; Measurement of adhesive strength of apatite formed on the surface of substrate using a Scotch Tape (T.M.) which is a product of Sumitomo 3M.

E. Test of apatite forming ability by dipping in simulated body fluid (SBF);

Specimen is dipped in 30 ml of SBF adjusted to pH 7.40 and temperature of 36.5° C., for various terms, wherein longest is 7 days. The specimen is picked out from said solution and washed by ultra pure water, then dried up at room temperature.

One example of aqueous solution which is supersaturated to apatite (simulated body fluid: SBF, having inorganic ion concentration nearly equal to human's plasma [T. Kokubo, H. Kushitani, S. Sakka, T. Kitsugi and T. Yamamuro, "Solutions able to reproduce in vivo surface-structure changes in bioactive glass-ceramic A-W", J. Biomed, Mater. Res.24, 721-734 (1996)]) is shown in Table 1.

TABLE 1

| ion | concentration/mM | |
| --- | --- | --- |
| | simulated body fluid pH 7.40 | plasma pH 7.20-7.40 |
| Na$^+$ | 142 | 142 |
| K$^+$ | 5.0 | 5.0 |
| Mg$^{2+}$ | 1.5 | 1.5 |
| Ca$^{2+}$ | 2.5 | 2.5 |
| Cl$^-$ | 148.8 | 103.8 |
| HCO$_3^-$ | 4.2 | 27.0 |
| HPO$_4^{2-}$ | 1.0 | 1.0 |
| SO$_4^{2-}$ | 0.5 | 0.5 |

EXAMPLE

The present invention will be illustrated more in detail according to Examples. These Examples are intending to make the present invention more clear and not restricting the scope of claims of the present invention.

Example 1

Preparation of Specimen

Organic polymer substrates are prepared by press molding at 90 kgf/cm$^2$ pressure for 10 minutes at adequate temperature for each resin, namely, 180° C. for polyethylene (PE), 270° C. for polyetyleneterephathalate (PET), 230° C. for Nylon 6 (N-6) and 210° C. for ethylene-vinylalcohol copolymer (EVOH) of Comparative Example.

Materials shown in Table 2 are used for the preparation of titania solution.

Solution containing TiPT (3.8687 g) and half weight of C$_2$H$_5$OH (2.9 g) are prepared, and solution consisting of residue half weight of C$_2$H$_5$OH (2.9 g), water (0.2450 g) and nitric acid (0.0858 g) is added to said solution by cooling with ice to 0-10° C. so as to hydrolysis and a titania gel solution is prepared.

Each specimens prepared by press molding are subjected to titania solution treatment by dipped in 10 g of titania gel solution kept at 25° C. for 24 hours. After dipped, specimens are pulled out by 2 cm/minute speed and dried in a dryer at 80° C. for 1 day and above mentioned press molding is carried out and titania solution treated specimens (S) are prepared.

TABLE 2

| Molar ratio of each component at the preparation of titania solution | | | |
| --- | --- | --- | --- |
| Ti(OiC$_3$H$_7$)$_4$(TiPT) | H$_2$O | C$_2$H$_5$OH | NHO$_3$ |
| 1.0 | 1.0 | 9.25 | 0.1 |

For the purpose to provide an apatite forming ability to a titania gel layer of prepared titania solution treated specimens, said titania solution treated specimens are dipped into 10 mL of 0.1M hydrochloric acid aqueous solution at 80° C. for 8 days and transformed said titania gel layer to a titanium oxide layer having an apatite layer forming ability by contact with supersaturated aqueous solution to apatite.

Figure 3:
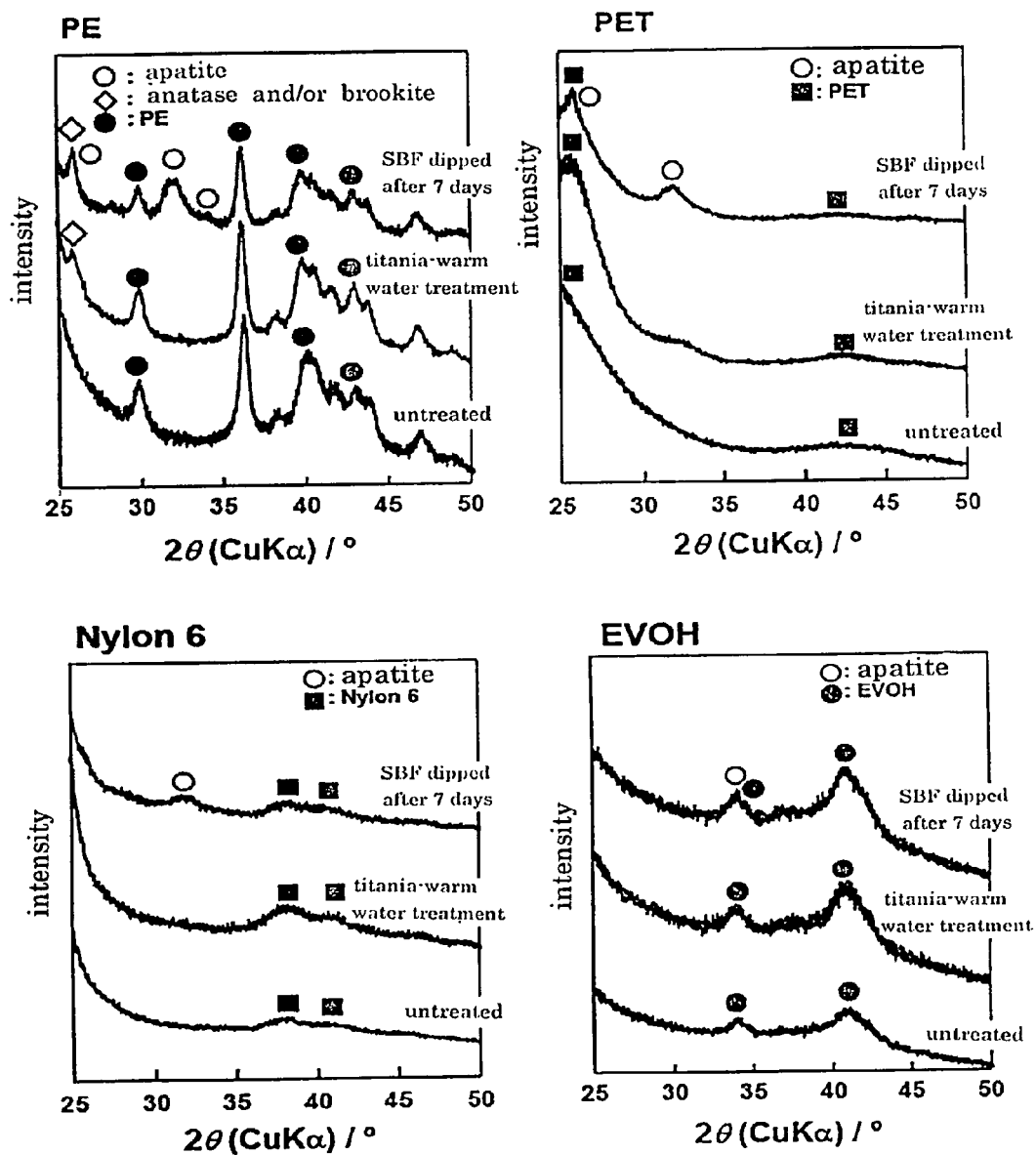
FIG. 3 indicates TF-XRD (Thin film X-ray diffraction) pattern of specimens of polyethylene (PE), polyester (PET), Nylon 6 and ethylene-vinylalcohol copolymer (EVOH, Comparative Example) base material which are treated by titania solution-warm water of FIG. 1 then dipped in SBF ○ is a detected pattern of a formed apatite, ◇ is a detected pattern of anatase and/or brookite structure, ▄ is a detected pattern of PE or EVOH and ■ is a detected pattern of PET or Nylon.

In FIG. 3, thin film X ray diffraction pattern of PE, PET, EVOH and Nylon-6, which are treated by titania solution and treated by followed warm water treatment without silane coupling agent treatment (SC), and are dipped in said SBF for 8 days are shown. In the case of PE, by titania-warm water treatment, peak belonging to anatase and/or brookite can be observed. After 7 days from SBF dipping, a peak belonging to apatite is observed in all specimens.

In FIG. 4, FE-SEM pictures of PE, PET, EVOH and Nylon-6 which are treated by titania solution and treated by followed warm water treatment without SC treatment and are dipped into SBF for 2 or 7 days are shown. A thin layer is formed by titania-warm water solution treatment. By EDS measurement, it becomes clear that this layer contains titanium. Accordingly, it is understood that a titania layer can be formed on the surface of specimen by directly carrying out titania-warm water treatment without SC treatment. After 2 days from SBF dipping, almost uniform apatite layer is formed on the surface of PE, PET and Nylon-6, however, on the surface of EVOH apatite layer is not formed. After 7 days from the dipping, apatite is formed on the surface of EVOH too, however the amount of it is very few.

In FIG. 5, FE-SEM pictures of the surface of specimens after removing test by a Scotch Tape (T.M.) are shown. In cases of PE, PET and Nylon-6, apatite is not removed by the removing test, while in a case of EVOH, apatite is removed from the substrate.

POSSIBILITY FOR THE INDUSTRIAL APPLICABILITY

The titanium oxide-organic polymer composite material of the present invention is to provide an artificial bone material which has apatite forming ability on the surface of a base material and is excellent in bonding strength between titanium oxide membrane and base material, which is prepared by using polyolefin, polyester or nylon as a base material, carrying out a treatment by titania solution which forms titania gel on the surface of the base material, which is developed by the inventors of the present invention, and a dipping treatment of said formed titania gel in warm water of 50° C. to 95° C., or solution of room temperature to 95° C. to which acid is added, or transforming said formed titania gel to titanium oxide membrane having forming ability of apatite of similar Ca/P atom ratio as to apatite of mammalian's bone in supersaturated aqueous solution to apatite or in body fluid of mammalian without treating the surface of base material by previous treatment such as SC treatment. That is, the present invention has an industrial applicability.

The invention claimed is:

1. A method for producing a titanium oxide-organic polymer composite material for artificial bone comprising the steps of:
   forming a titania solution by adding a solution consisting of acidic alcohol and water into an alcohol solution of titaniumtetraalkoxide,
   providing an organic polymer base material which includes a polymer selected from the group consisting of polyolefin, polyester and nylon, and does not have an active group selected from the group consisting of hydroxyl groups or derivatives thereof, thiol groups, aldehyde groups and amino groups,
   forming titania gel on the surface of the base material by dipping the base material into a solution of the titania solution which is at a temperature of 0° C. to 50° C. for several seconds to 1 week, and drying the base material with the titania gel formed on its surface,
   treating the titania gel that has formed on the surface of the base material by dipping the base material with the titania gel formed on its surface into hot water of 50° C. to 95° C. or a solution of room temperature to 95° C. to which acid is added for an effective period of time to form a titanium oxide membrane on the base material and to obtain the titanium oxide-organic polymer composite material for artificial bone, wherein the titanium oxide membrane has activity to form an apatite in mammalian body fluid, and wherein the apatite has a similar Ca/P atom ratio to an apatite of mammalian bone,
   with the proviso that an intermediate layer is not formed on the base material by contacting the base material with a silane coupling agent to form an intermediate layer.

2. The method for producing a titanium-oxide organic polymer composite material for artificial bone of claim 1, wherein titaniumtetraalkoxide is tetraisopropyltitanate, alcohol is ethanol and acid is inorganic acid.

3. The method for producing a titanium-oxide organic polymer composite material for artificial bone of claim 1, wherein polyolefin is low-density polyethylene, polyester is polyethyleneterephthalate and nylon is 6-nylon.

4. The method for producing a titanium-oxide organic polymer composite material for artificial bone of claim 1, further comprising forming the titania solution by adding a solution consisting of acidic alcohol and water into a solution of titaniumtetraalkoxide and alcohol and maintaining the temperature at 0° C. to 10° C.

5. The method for producing a titanium oxide-organic polymer composite material for artificial bone of claim 2, wherein polyolefin is low-density polyethylene, polyester is polyethyleneterephthalate and nylon is 6-nylon.

6. The method for producing a titanium oxide-organic polymer composite material for artificial bone of claim 2, wherein forming the titania solution further comprises adding a solution consisting of acidic alcohol and water to a solution of titaniumtetraalkoxide and alcohol and maintaining the temperature at 0° C. to 10° C.

7. The method for producing a titanium oxide-organic polymer composite material for artificial bone of claim 3, wherein forming the titania solution further comprises adding a solution consisting of acidic alcohol and water to a solution of titaniumtetraalkoxide and alcohol and maintaining the temperature at 0° C. to 10° C.

8. A method for producing a composite material for artificial bone comprising the steps of:
   producing a titanium oxide-organic polymer composite material for artificial bone by forming a titania solution by adding a solution consisting of acidic alcohol and water into alcohol solution of titaniumtetraalkoxide,
   providing an organic polymer base material which includes a polymer selected from the group consisting of polyolefin, polyester and nylon, and does not have an active group selected from the group consisting of hydroxyl groups or derivative thereof, thiol groups, aldehyde groups and amino groups,
   forming titania gel on the surface of the base material by dipping the base material into a solution of the titania solution which is at a temperature of 0° C. to 50° C. for several seconds to 1 week,
   drying the base material with the titania gel formed on its surface, and
   treating the titania gel that has formed on the surface of the base material by dipping the base material with the titania gel formed on its surface into hot water of 50° C. to 95° C. or solution of room temperature to 95° C. to which acid is added for an effective period of time to form a titanium oxide membrane on the base material and to obtain the titanium oxide-organic polymer composite material for artificial bone, wherein the titanium oxide membrane has activity to form an apatite in mammalian body fluid, and wherein the apatite has a similar Ca/P atom ratio to an apatite of mammalian bone,
   with the proviso that an intermediate layer is not formed on the base material by contacting the base material with a silane coupling agent to form an intermediate layer.

9. The method for producing a composite material for artificial bone of claim 8, wherein titaniumtetraalkoxide is tetraisopropyltitanate, alcohol is ethanol and acid is inorganic acid.

10. The method for producing a composite material for artificial bone of claim 8, wherein polyolefin is low-density polyethylene, polyester is polyethyleneterephthalate and nylon is 6-nylon.

11. The method for producing a composite material for artificial bone of claim 8, wherein forming the titania solution further comprises adding a solution consisting of acidic alcohol and water to a solution of titaniumtetraalkoxide and alcohol and maintaining the temperature at 0° C. to 10° C.

12. The method for producing a composite material for artificial bone of claim 9, wherein polyolefin is low-density polyethylene, polyester is polyethyleneterephthalate and nylon is 6-nylon.

13. The method for producing a composite material for artificial bone of claim 9, wherein forming the titania solution further comprises adding a solution consisting of acidic alcohol and water to a solution of titaniumtetraalkoxide and alcohol and maintaining the temperature at 0° C. to 10° C.

14. The method for producing a composite material for artificial bone of claim 10, wherein forming the titania solution further comprises adding a solution consisting of acidic alcohol and water to a solution of titaniumtetraalkoxide and alcohol and maintaining the temperature at 0° C. to 10° C.

15. The method for producing a composite material for artificial bone of claim 12, wherein forming the titania solution further comprises adding a solution consisting of acidic alcohol and water to a solution of titaniumtetraalkoxide and alcohol and maintaining the temperature at 0° C. to 10° C.

* * * * *